United States Patent [19]

Buchanan

[11] Patent Number: 4,823,781
[45] Date of Patent: Apr. 25, 1989

[54] METHOD AND APPARATUS FOR PERCUTANEOUS FRACTURE REDUCTION AND FIXATION

[76] Inventor: William J. Buchanan, 118 Montreal St., Playa del Rey, Calif. 90293

[21] Appl. No.: 69,048

[22] Filed: Jul. 2, 1987

[51] Int. Cl.$^4$ .............................................. A61F 5/04
[52] U.S. Cl. .............................. 128/92 Z; 128/92 ZY; 128/92 ZW
[58] Field of Search ........... 128/92 Z, 92 ZZ, 92 ZY, 128/92 ZK, 92 ZW, 92 Y, 92 YF, 92 YE, 92 YD, 92 YC

[56] References Cited

U.S. PATENT DOCUMENTS

| | | | |
|---|---|---|---|
| 2,055,024 | 9/1936 | Bittner, Jr. | 128/92 Z X |
| 2,250,417 | 7/1941 | Ettinger | 128/92 Z |
| 2,391,537 | 12/1945 | Anderson | 128/92 Z |
| 2,406,987 | 9/1946 | Anderson | 128/92 ZW |
| 4,135,505 | 1/1979 | Day | 128/92 Z |
| 4,273,116 | 6/1981 | Chiquet | 128/92 ZW X |
| 4,360,012 | 11/1982 | McHarrie | 128/92 ZW X |
| 4,365,624 | 12/1982 | Jaquet | 128/92 Z |
| 4,488,542 | 12/1984 | Helland | 128/92 Z |
| 4,628,921 | 12/1986 | Rousso | 128/92 Z |
| 4,628,922 | 12/1986 | Dewar | 128/92 Z |

FOREIGN PATENT DOCUMENTS 906545 2/1982 U.S.S.R. ............................ 128/92 Z

Primary Examiner—Robert A. Hafer
Assistant Examiner—Kevin G. Rooney
Attorney, Agent, or Firm—Blakely, Sokoloff, Taylor, Zafman

[57] ABSTRACT

A method and apparatus to percutaneously reduce a bone fracture and to maintain reduction during percutaneous, limited open, or open fixation of the fracture. The apparatus comprises a movable part threadably engaged with a fixed part. The fixed part of the apparatus attaches to a rigid frame surrounding the site of the fracture. A surgical pin is threaded into a bone fragment and secured to the moveable part of the apparatus. Additional pins are threaded into the bone and rigidly secured to the frame. The apparatus allows controlled axial movement of the pin relative to the frame. A medical procedure employs this apparatus to accurately reduce a fracture percutaneously while percutaneous or limited open fixation is performed.

12 Claims, 3 Drawing Sheets

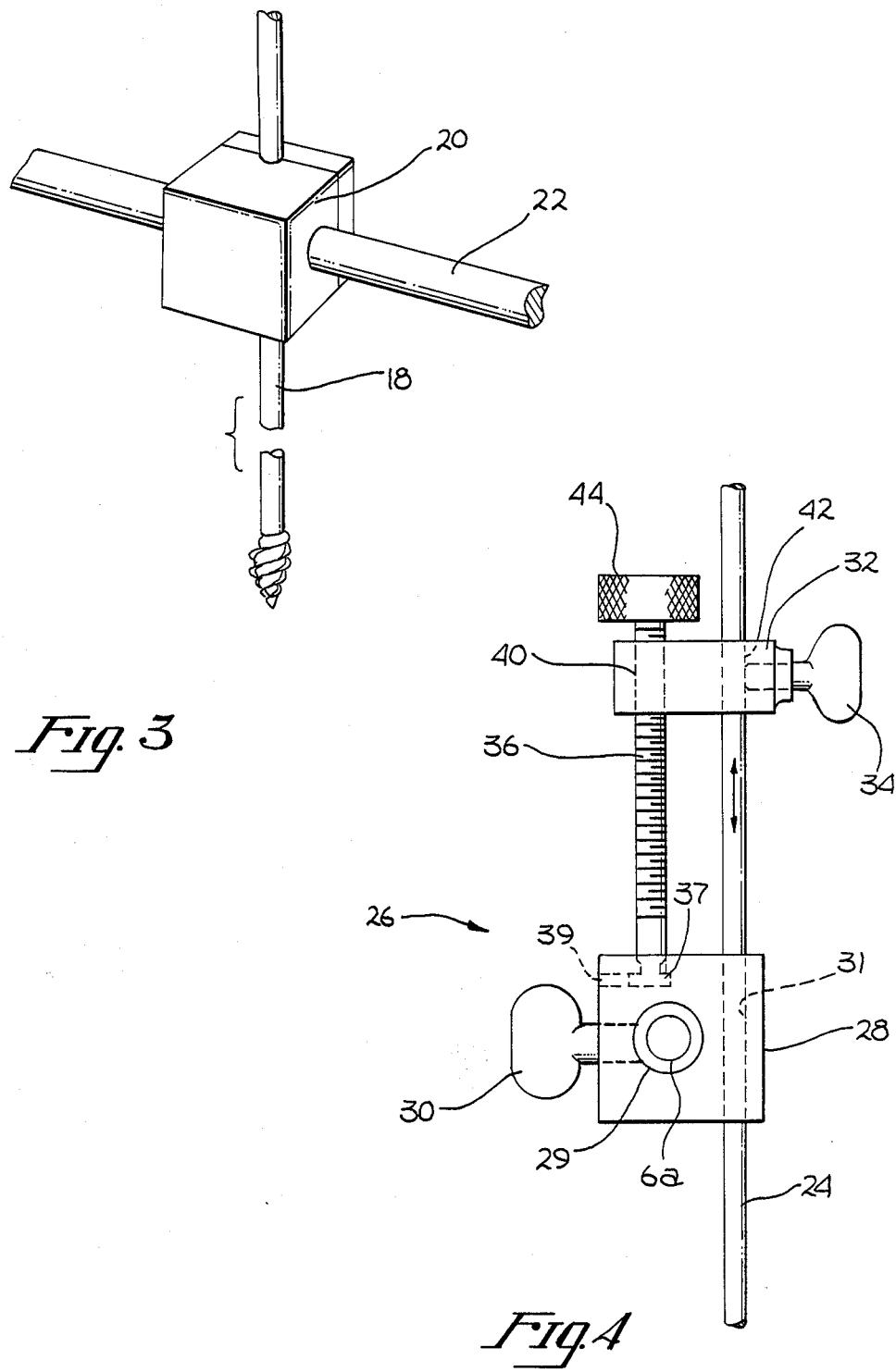

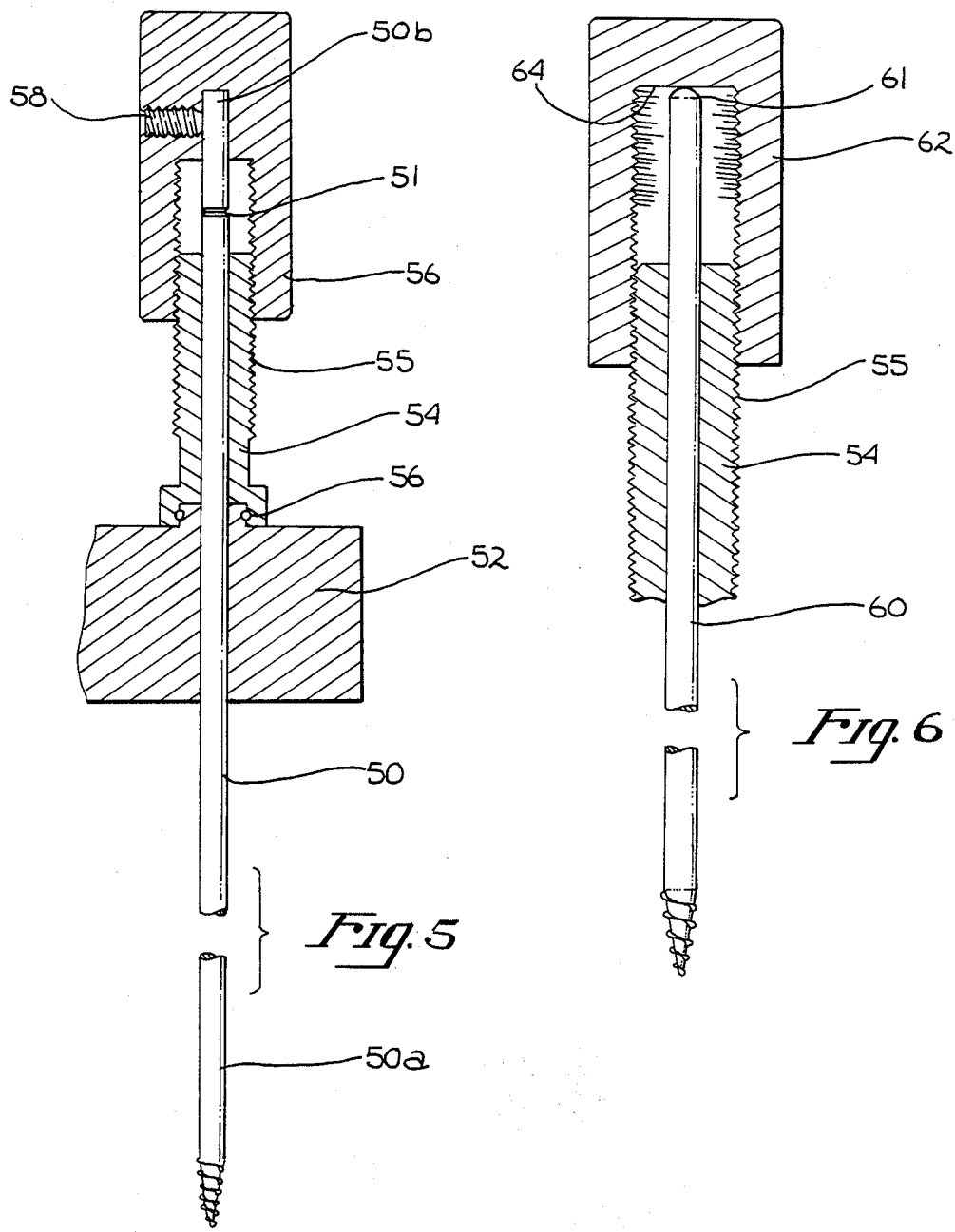

METHOD AND APPARATUS FOR PERCUTANEOUS FRACTURE REDUCTION AND FIXATION

BACKGROUND OF INVENTION (I.) Field of The Invention

The present invention relates to the field of orthopedic surgery and, more particularly, to a method and apparatus for bone fracture reduction and fixation.

(II.) Prior Art

Existing techniques for fracture reduction and fixation in cases requiring artificial fixation of a bone fragment involve extensive surgical procedures. Typically, a large incision in the vicinity of the fracture is necessary to expose the fracture and facilitate location of the bone fragment. The fragment is then mechanically reattached to the bone from which it was broken away by means of fasteners, for example, plates and screws. Such surgery is a lengthy procedure, generally 1–3 hours, subjecting the patient to the inherent hazards and discomfort of such procedures. The size of the incision generally requires the use of a tourniquet to control bleeding during surgery. Furthermore, extensive soft tissue stripping is frequently necessitated which creates a substantial risk of infection and non-union of the fracture.

Existing non-surgical techniques for fracture immobilization and partial reduction employ a frame-like apparatus with extended screws mounted thereto for attachment to the fracture. This apparatus, or frame, is constructed of various standard components to achieve the particular configuration required by the geometry of the frame to be immobilized. These components include sections of round tubing of various lengths. Interconnection of the lengths of tubing and attachment of other components is facilitated by blocks which clamp to the external surface of the tubing. These blocks consist of a body and a clevis. They are drilled with a hole slightly larger in diameter than the diameter of the tube. The body of the block has two threaded studs perpendicular to the axis of the hole extending from opposite faces of the body. A locknut placed over one of these studs engages the face of the clevis, thereby clamping the block to the length of tubing. Other components are then attached to the other stud.

One such component is a tie bar which permits the attachment of one length of tubing to another. Another component is a clamp which engages a cylindrical stainless steel pin. The pin is threaded at one end in the manner of a common wood screw. Such pins are screwed into holes which are drilled into the main segment of the fractured bone and into one or more bone fragments. The pins, the clamps and the blocks can be freely positioned with respect to one another and with respect to the tubular frame. Pins attached to the bone and bone fragments may be manipulated to any desired position and then rigidly secured to the frame members, thereby immobilizing the fracture and positioning the bone and bone fragment for healing. The device is then maintained in position for several weeks until the bone is, at least, partially heeled. Eventually, the prior art device is removed and more conventional fixation devices, such as a cast, are used to complete the therapeutic treatment.

Partial reduction may be accomplished by positioning the pins on the frame so as to reposition the bone fragments relative to the bone. However, such partial reduction cannot be accurately controlled. Thus, such prior art external fixators are not useful for reduction of fractures requiring significant accuracy, such as articular fractures. Furthermore, the external fixator utilizes no application of internal fixation. The patient is thus confined by the apparatus for an extended period of time (as long as several weeks) as healing proceeds.

SUMMARY OF THE INVENTION

It is an object of the present invention to provide a means for accurately controlled percutaneous fracture reduction, thereby achieving superior reductions in some situations. It is a further object of the invention to employ such a percutaneous fracture reduction in combination with internal fixation, thereby obviating the need for lengthy confinement of the patient.

It is also an object of the present invention to eliminate or significantly reduce the extent of the surgical opening required to achieve fracture reduction and fixation, thereby eliminating or reducing the need for a tourniquet and significantly reducing blood loss. Soft tissue stripping is minimized, thus reducing the risk of subsequent infection, enhancing post-procedure fracture stability and increasing the potential for fracture healing. It is a further object of the invention to significantly reduce the duration of the reduction and fixation procedure, thereby reducing the surgical risk and discomfort to the patient.

The invention which achieves these objects is a method and apparatus for percutaneously reducing features and maintaining reduction during percutaneous or limited open fixation of the fracture.

The device permits attachment of a pin, such as a stainless steel pin with screw threads at one end similar to that which is commonly used for fracture immobilization, to a rigid frame, such as one constructed of stainless steel tubing, so as to permit accurately controlled movement of the pin in a direction substantially parallel to its axis. In one embodiment, this device comprises a clamp for attachment to a frame member and a clamp for attaching the pin. Rotation of a threaded screw causes axial movement of the pin relative to the rigid frame thereby controllably advancing or withdrawing the pin to reduce the fracture.

In a medical procedure, a frame, as commonly used for external fracture immobilization, is rigidly attached to the main segment of the fractured bone by one or more percutaneously inserted pins. Additional pins are percutaneously inserted into the bone fragments and, with the aid of direct or indirect visualization, are manipulated so as to initially reduce the fracture. These pins are then rigidly locked to the frame. The device described previously is employed to complete and maintain reduction while percutaneous or limited open fixation is performed.

BRIEF DESCRIPTION OF DRAWINGS

FIG. 3 is an enlarged detailed view of a block for securing surgical pins in the invented procedure.

FIG. 4 is a detailed view of a preferred embodiment of the present invention.

FIG. 5 is an enlarged sectional view of an alternative embodiment of the present invention.

FIG. 6 is an enlarged sectional view of another alternative embodiment of the present invention.

DETAILED DESCRIPTION OF THE PREFERRED EMBODIMENTS

Figure 1:
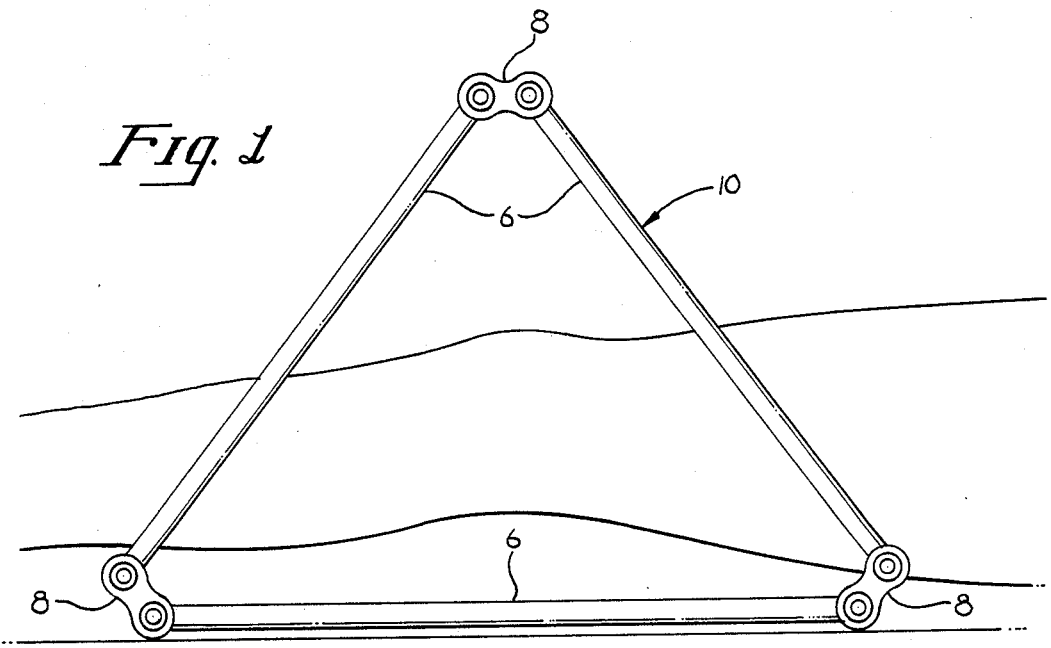
FIG. 1 is a side view of a prior art frame with which the present invention may be used.

FIG. 1 shows a frame 10 formed of lengths 6 of tubular stainless steel or other suitable material interconnected with articulated joints 8 which allow the frame to be assembled in various configurations. Such frame components are commonly available to orthopedic specialists. The frame is constructed and positioned relative to the site of the frame in somewhat the same manner as for conventional external fracture immobilzation procedures. The frame is configured so that the fracture site is accessible to X-ray imaging and so that a pin, such as pin 24, may be attached to the frame perpendicular to the fracture line.

Figure 2:
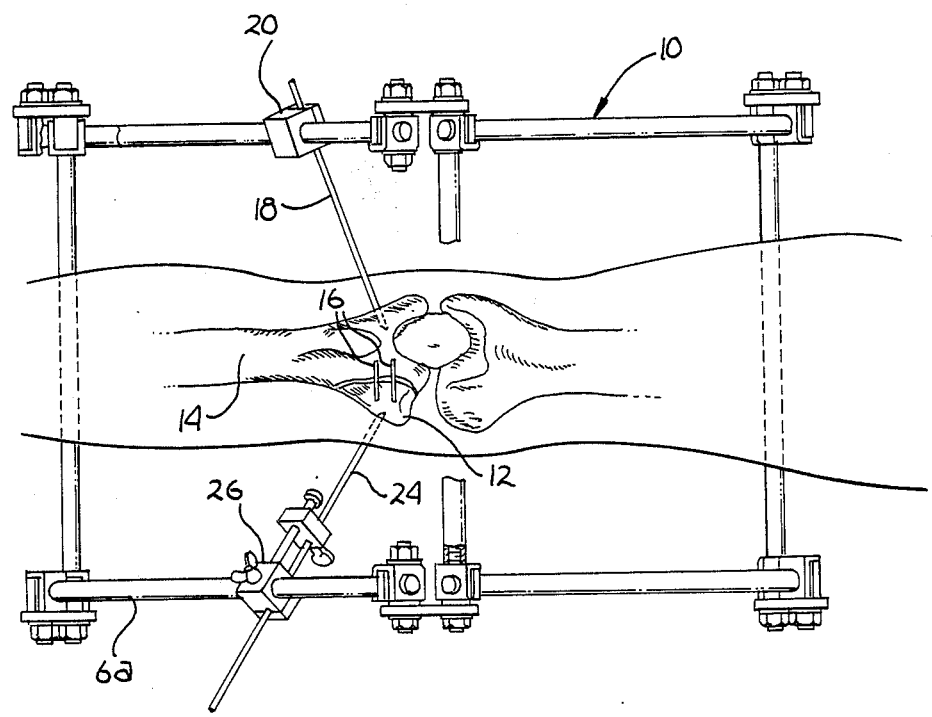
FIG. 2 is a plan view illustrating the invented fracture reduction and fixation procedure.

Referring now to FIG. 2, compressor 26 is shown attached to member 6a of frame 10. Compressor 26 grasps pin 24, which may be a pin such as one made of stainless steel or other suitable material with screw threads at one end thereof. Such pins are commonly used for fracture immobilization procedures. Pin 24 is secured relative to frame 10 by means of compressor 26 which is more fully illustrated in FIG. 4.

Frame member 6a passes through hole 29 in block 28 allowing block 28 to be freely positioned along the length of frame member 6a and rotated about the axis thereof. Block 28 is secured to frame member 6a in a desired position and orientation by means such as thumb screw 30. Hole 31 extends through block 28 in a direction generally orthogonal to hole 29 and has a diameter such that pin 24 slides freely therewithin in the directions indicated by the arrows in FIG. 4.

Threaded screw 36 is parallel to pin 24 and is captively held in an axial direction by block 28 but is free to rotate about its axis. Screw 36 may be suitably held by means such as shoulder 37 which engages slot 39 in block 28. The threads of screw 36 engage mating threads in hole 40 of block 32.

Hole 42 in block 32 has a diameter approximately equal to that of hole 31 in block 28 so that pin 24 passes freely therethrough. Pin 24 may be secured to block 32 by means such as thumb screw 34.

Rotation of screw 36 by means of knob 44 causes block 32 to travel linearly along the threads of screw 36. When pin 24 is secured to block 32, rotation of screw 36 will thus cause pin 24 to travel axially in the directions indicated by the arrows in FIG. 4. It can therefore be seen that axial movement of pin 24 may be accurately controlled by knob 44 and, furthermore, that controlled pressure may be applied to pin 24 to urge it axially against a resisting force such as is required to achieve reduction of a fracture.

FIG. 5 illustrates an alternative embodiment of compressor 26. This embodiment employs threaded pin 50 which comprises threaded section 50a and splined section 50b. Sections 50a, 50b are coupled axially by coupling 51 so as to permit independent rotation of the two sections about their common axis. Block 52 may be secured to a tubular frame member as explained in the previously described embodiment. Compressor sleeve 54 is secured to block 52 by means such as snap fitting 56. Sleeve 54 is drilled to receive pin 50 so that pin 50 slides freely in an axial direction within sleeve 54. threaded portin 55 of sleeve 54 engages mating threads in compressor handle 56. Handle 56 engages splined section 50b of pin 50 and is secured thereto by means such as set screw 58.

It can be seen that rotation of handle 56 will cause handle 56 to travel linearly along the threads of sleeve 54 thereby causing pin 50 to travel axially in the directions indicated by the arrows in FIG. 5. Threaded section 50a of pin 50 does not rotate about its axis as handle 56 is rotated by virtue of coupling 51. This embodiment offers the advantages of having handle 56 disposed coaxially with pin 50 and allowing positive bi-directional movement of pin 50.

Yet another embodiment of compressor 26 is illustrated in FIG. 6. In this embodiment, pin 60 is not jointed and may be a pin such as is commonly available for orthopedic procedures. Sleeve 54 is as described previously. Threaded portion 55 of sleeve 54 engages mating threads in compressor handle 62. Bearing surface 64 of handle 62 contacts end 61 of pin 60 and transmits axial force from handle 62 to pin 60. Using right-handed threads, as handle 62 is rotated clockwise, as viewed looking towards sleeve 54, it travels linearly along the threads of sleeve 54 thereby causing pin 60 to travel axially in the direction indicated by the arrow in FIG. 6.

Referring again to FIG. 2, frame 10 is shown positioned around a fracture in which bone fragment 12 has separated from bone 14. This figure particularly illustrates an articular fracture of the tibia, however, it is understood that the invention is equally applicable to other types of fractures and fractures of other bones. The object of the disclosed procedure is to accurately position bone fragment 12 in proper relation to bone 14, thereby reducing the fracture so that the fragment can be rettached to the bone by means of fasteners 16. While fracture reduction and fixation of a single bone fragment is described, it can readily be seen that the disclosed procedure is equally applicable to fractures involving a plurality of bone fragments.

To begin the procedure, pin 18 is percutaneously attached to bone 14 by means of threads at one end. Once pin 18 has engaged the bone, it is locked in position relative to frame 10 by means of block 20, which is more fully illustrated in FIG. 3. Block 20 is free to move axially along tubular frame member 22 and to rotate about the axis of the frame member. Block 20 incorporates means for locking it in any desired position on the frame. Pin 18 is likewise free to move axially through block 20 and to rotate about its axis. Block 20 also incorporates means for locking pin 18 in any desired position. Such pin and block are also commonly available to orthopedic specialists.

Bone fragment 12 is located by direct or indirect visualization, such as by x-ray, image intensification or arthroscopy. Fragment 12 is then percutaneously engaged by the threaded end of pin 24. A manipulating handle may be attached to the non-threaded end of pin 24 to enable controlled movement of the bone fragment. With the aid of the chosen visualization technique, pin 24, with bone fragment 12 attached thereto, is manually positioned so that partial reduction of the fracture is accomplished.

Once the bone fragment has been manually positioned so that partial reduction of the fracture is accomplished, compressor 26 is rigidly secured to the frame. Compressor 26 is then employed as described above in connection with the several embodiments disclosed herein to cause pin 24 to move axially in a direction approximately perpendicular to and towards the fracture interface. This movement causes compression of bone fragment 12 against bone 14 along the fracture interface, thereby completing reduction of the fracture.

When the fracture is fully reduced by the method thus far described, fixation is achieved by insertion of fasteners 16. Such fasteners may be inserted percutaneously or through limited surgical incisions. The frame 10 may be used for guiding the drill and fastener placement. When fixation is achieved, pins 18 and 24 are removed and frame 10 is disassembled.

Although this invention has been described in terms of certain preferred embodiments, other embodiments that are apparent to those of ordinary skill in the art are also within the scope of this invention. It is to be understood that the terminology used is for the purpose of description and not of limitation. Accordingly, the scope of the invention is intended to be limited only by the appended claims.

I claim:

1. An improved fracture reduction apparatus of the type in which at least one first pin and at least one second pin are secured to a rigid frame, said first pin for attachment to a fractured bone and said second pin having a fixed proximal end for attachment to a bone fragment, wherein the improvement comprises:
    means for securing said second pin to the frame, said securing means including means for imparting controlled motion to said second pin relative to the frame such that said second pin moves substantially axially without rotation about its axis; and
    means for fixing said second pin in a predetermined position;
    wherein the means for imparting motion comprises:
    a first block having means for attachment to the frame;
    a second block having a first hole therethrough for slideable insertion of said second pin;
    locking means for securing said second pin within said second block; and
    a threaded screw axially captive in said first block and engaging mating threads in a second hole in said second block, said second hole approximately parallel to said first hole;
    whereby rotation of said threaded screw causes axial movement of said second pin.

2. An improved fracture reduction apparatus of the type in which at least one first pin and at least one second pin are secured to a rigid frame, said first pin for attachment to a fractured bone and said second pin having a fixed proximal end for attachment to a bone fragment, wherein the improvement comprises:
    means for securing said second pin to the frame, said securing means including means for imparting controlled motion to said second pin relative to the frame such that said second pin moves substantially axially without rotation about its axis; and
    means for fixing said second pin in a predetermined position;
    wherein the second pin comprises a threaded proximal section and distal section, said proximal and distal sections coupled axially to allow independent rotation of each section about a common axis.

3. The improved fracture reduction apparatus as recited in claim 2, wherein the means for imparting motion comprises:
    a block having means for attachment to the frame;
    a sleeve coupled to said block having a hole therethrough for slidable insertion of said second pin and a threaded cylindrical outer surface;
    a handle having a cylindrical cavity threaded for mating engagement with said threaded outer surface of said sleeve and adapted to receive said distal section of said second pin; and
    locking means for securing said handle to said distal section of said second pin.

4. An improved fracture reduction apparatus of the type in which at least one first pin and at least one second pin are secured to a rigid frame, said first pin for attachment to a fractured bone and said second pin having a fixed proximal end for attachment to a bone fragment, wherein the improvement comprises:
    means for securing said second pin to the frame, said securing means including means for imparting controlled motion to said second pin relative to the frame such that said second pin moves substantially axially without rotation about its axis; and
    means for fixing said second pin in a predetermined position;
    wherein the means for imparting motion comprises;
    a block having means for attachment to the frame;
    a sleeve coupled to said block having a hole therethrough for slideable insertion of said second pin and a threaded cylindrical outer surface; and
    a handle having a cylindrical threaded cavity for mating engagement with said threaded outer surface of said sleeve and a bearing surface at a distal end of said cavity adapted to engage a distal end of said second pin.

5. A medical procedure for performing fracture reduction and fixation of a fractured bone having a main segment and at least one bone fragment, said medical procedure comprising:
    (a) providing a rigid frame adjacent the fracture bone;
    (b) attaching a first pin to the main segment of the fracture bone;
    (c) securing the first pin rigidly to the frame;
    (d) attaching a second pin to the bone fragment;
    (e) manipulating the second pin to partially reduce the frame;
    (f) securing the second pin to the frame so as to still allow axial movement of the second pin;
    (g) imparting controlled motion to the second pin substantially along its axis to complete reduction of the fracture; and
    (h) fixing the bone fragment to the main segment of the bone with a fastener while fracture reduction is maintained by said second pin.

6. The medical procedure as recited in claim 5 wherein the first pin in step (b) is attached percutaneously.

7. The medical procedure as recited in claim 5 wherein the second pin in step (d) is attached percutaneously.

8. The medical procedure as recited in claim 5 further comprising the additional step of visualizing the fracture bone and a surrounding area.

9. The medical procedure as recited in claim 5 wherein fixation is performed percutaneously.

10. The medical procedure as recited in claim 5 wherein fixation is performed through a surigical opening.

11. The medical procedure as recited in claim 5 further comprising the additional step of removing the frame immediately after fixation.

12. A surgical pin for use in a fracture reduction and fixation procedure employing a surgical frame having a plurality of frame members, said pin comprising:
   a threaded proximal section for insertion into a bone fragment;
   a distal section having a common axis with said proximal section and rotatably coupled thereto so as to preclude axial separation of said proximal and distal sections;
   a sleeve having a threaded cylindrical outer surface and a hole extending axially therethrough, said hole being adapted for slidable insertion of said proximal section, said sleeve including means disposed at a proximal end thereof for rigid attachment to one of said surgical frame members; and
   a handle having a cylindrical cavity opening at a proximal end of said handle, said cavity threaded for mating engagement with said threaded outer surface of said sleeve, said handle including means disposed at a distal end thereof for gripping said distal section.

* * * * *

UNITED STATES PATENT AND TRADEMARK OFFICE
CERTIFICATE OF CORRECTION

PATENT NO. : 4,823,781

DATED : 04-25-89

INVENTOR(S) : Buchanan

It is certified that error appears in the above-identified patent and that said Letters Patent is hereby corrected as shown below:

| Column | Line | |
|---|---|---|
| 1 | 34 | delete "frame", insert --fracture-- |

Signed and Sealed this

Sixteenth Day of January, 1990

Attest:

JEFFREY M. SAMUELS

*Attesting Officer*     *Acting Commissioner of Patents and Trademarks*